(12) United States Patent
Sharma et al.

(10) Patent No.: US 7,429,125 B2
(45) Date of Patent: Sep. 30, 2008

(54) SYSTEM AND METHOD FOR CANTILEVER BASED CALORIMETRIC ANALYSIS

(75) Inventors: Manish Sharma, Palo Alto, CA (US); Alison Chaiken, Palo Alto, CA (US); Alex Bratkovski, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 170 days.

(21) Appl. No.: 11/270,690

(22) Filed: Nov. 9, 2005

(65) Prior Publication Data

US 2007/0104245 A1 May 10, 2007

(51) Int. Cl.
*G01K 17/00* (2006.01)
(52) U.S. Cl. ........................................................ 374/31
(58) Field of Classification Search .................. 374/31; 436/147
See application file for complete search history.

(56) References Cited

U.S. PATENT DOCUMENTS

| | | | | |
|---|---|---|---|---|
| 5,445,008 | A * | 8/1995 | Wachter et al. | ............ 73/24.06 |
| 5,719,324 | A * | 2/1998 | Thundat et al. | ............ 73/24.01 |
| 5,977,544 | A * | 11/1999 | Datskos et al. | ........... 250/338.1 |
| 6,096,559 | A | 8/2000 | Thundat et al. | |
| 6,289,717 | B1 * | 9/2001 | Thundat et al. | .............. 73/23.2 |
| 6,312,959 | B1 * | 11/2001 | Datskos | ....................... 436/147 |
| 6,575,020 | B1 * | 6/2003 | de Charmoy Grey et al. | ......................... 73/54.23 |
| 6,772,070 | B2 | 8/2004 | Gilmanshin et al. | |
| 6,805,839 | B2 * | 10/2004 | Cunningham et al. | .... 422/82.12 |
| 7,141,385 | B2 * | 11/2006 | Bottomley et al. | ........... 435/7.4 |
| 2005/0037499 | A1 * | 2/2005 | Ramberg et al. | ................ 436/3 |
| 2005/0105427 | A1 * | 5/2005 | Cookson et al. | .......... 369/47.31 |
| 2007/0145966 | A1 * | 6/2007 | Shekhawat et al. | ......... 324/71.1 |

OTHER PUBLICATIONS

Hagan et al., "Nanomechanical Forces Generated by Surface Grafted DNA", 106 J. Phys. Chem 10163 (2002).
Lavrik et al., "Cantilever transducers as a platform for chemical and biological sensors", 74 Review of Scientific Instruments, 2229 (2004).
Fritz et al., "Translating Biomolecular Recognition into Nanomechanics", 338 Science 316 (2000).

* cited by examiner

*Primary Examiner*—Edward Lefkowitz
*Assistant Examiner*—Megann E Vaughn (57) ABSTRACT

A system for performing cantilever based calorimetric analysis system. A laser device is configured to emit a beam of laser energy along a beam pathway reaching from the laser device to a microcantilever. The microcantilever presents a reflective target area for the laser beam. The microcantilever deflects in response to heat. A material is provided adjacent to the target area. The material receives heat energy from the laser beam. A detector is positioned on a beam return pathway. The detector is configured to sense laser energy from the beam return pathway and provide a data single that represents calorimetric data from the material. Control circuitry is also provided to receive the data signal from the detector and process the data signal according to program logic for providing a differential scanning calorimetric analysis of the calorimetric data. An associated method of use is also provided.

7 Claims, 5 Drawing Sheets

SYSTEM AND METHOD FOR CANTILEVER BASED CALORIMETRIC ANALYSIS

FIELD OF THE INVENTION

The present invention relates generally to the field of protein identification and, to a structure and method of forming a thin film device such as an inverter and or other device and circuit components.

BACKGROUND

With the completion of mapping the human genome, science has ushered in a new frontier of research and development. Scientists are now undertaking studies to understand the underlying proteins which make up the genetic code. Proteomics is the study of proteins which make up the twenty-three common amino acids that can be created from the nucleic acid bases of genomics. Proteomics can be much more complex than genomics due to the extremely large number of proteins that can be "spelled" by the twenty-three amino acids. Further, photometric assays are usually quantitative, providing information about the concentration of particular proteins, not just their mere presence or absence.

Two common macroscopic methods for purifying proteins are currently used. First, gel electrophoresis is a technique that involves electric-field induced migration of the proteins through gels. Electrophoresis can be inexpensive and is generally achieves high purity. However, it is slow since separation is based on diffusion of the proteins through a gel medium.

A second common method for protein identification is matrix-assisted laser desorption ionization (MALDI). MALDI is a mass spectroscopic, time-of-flight method based on laser desorption of bio-molecules in a vacuum chamber. While sensitive and capable of high purity, specific (due to many fragments of different masses from a given protein) and potentially quantitative, MALDI is a slow process and requires expensive, non-portable equipment.

Many new proteomic screening methods based on antibody-antigen binding have been developed using lithographic technology to design assays built into microchips. The microchips can contain devices designed to be coated with complementary antibodies which allow a specific protein to bind to the device.

These new assays have the advantage of being relatively fast and inexpensive, but they are applicable to generalized testing given their reliance on the availability of complimentary antibodies. In other words, if the proper binding antibody is not provided by the assays, the presence or absence of a protein requiring that particular binding antibody will remain unknown. When complimentary antibodies are not available, non-specific binding to the device may occur, but such binding is by no means a true indicator for identification.

Existing micro-cantilever based on-chip assays rely on optical detection of a static cantilever deflection when a protein unfolds. A laser, LED, or other optical source can be used to measure the amount of deflection, which can then be used to determine the specific types of proteins. When complex biological fluids, such as for example blood, are used rather than test solutions like buffered saline, optical opacity may be a serious problem and the entire analysis and identification process may be thwarted.

On-chip detection, identification and quantization of proteins in complex solutions such as blood are highly desirable for a large number of health monitoring and screening applications. For example, rapid home tests for HIV invention or pathogens in food could save countless lives. Portability of the test equipment for home use and field use beyond the confines of a laboratory is also highly desirable so as to expedite the identification of pathogens and identify the source so as to limit further exposure.

On-chip detection methods can be faster and cheaper than those involving high-vacuum systems or lasers. However, most on-chip tests identify proteins through observation of specific antibody binding reactions. When on-chip detectors utilize non-specific binding mechanisms, accuracy is lost as they lose the ability to identify specific proteins.

Microcantilever devices provide nanomechanical motion in response to thermal change. The microcantilevers have a high surface area to volume ratio, which permits detection of surface stresses that are too small for observation on a macroscale. The microcantilever devices are used in a wide variety of physical, chemical, and biological sensing applications, as reported by Lavrik et al., *Cantilever transducers as a platform for chemical and biological sensors*, 74 Review of Scientific Instruments, 2229 (2004).

The mode of action is to convert changes in Gibbs free energy into a mechanical response, for example, as reported by Hagen et al., *Nanomechanical Forces Generated by Surface Grafted DNA*, 106 J. Phys. Chem 10163 (2002). Analyte-adsorbate interactions and adsorbate-adsorbate interactions are known to induce mechanical responses, as reported by Fritz et al., *Translating Biomolecular Recognition into Nanomechanics*, 338 Science 316 (2000). A common type of microcantilever device is a silicon nitride beam, for example, of 200 μm thickness, with a gold layer deposited to perhaps ten percent of this thickness.

The transduction of a chemical signal into a mechanical response may occur according to Stoney's formula, which predicts a bending moment in the microcantilever device in response to surface stress. Microcalorimeter devices are available on commercial order, for example, from MicroCal, LLC of Northhampton, Md.

One type of microcalorimetry application is isothermal titration calorimetry. In this type of system, a syringe is used to inject an analyte, and an adiabatic shield surrounds two cells. One cell is a reference cell and the other is a sample cell that is positioned to receive the analyte. The two cells are maintained at a temperature differential where the reference cell is maintained at constant power and the sample cell is maintained by using power that is proportional to a temperature difference between the sample cell and the reference cell. The calorimetric behavior of the analyte is assessed as a difference between a calibration run (without the analyte) and a separate run with the analyte being present.

The ability to detect extremely small thermal changes provides a platform for investigation into chemical changes that were previously unquantifiable. In various examples, isothermal titration calorimetry has been used to study protein interactions including those for small molecules—enzyme inhibition, protein-carbohydrate, protein-protein, protein-lipid, protein-nucleic acid, protein folding, and protein stability. Isothermal titration calorimetry has also been used to study nucleic acids including nucleic acid-small molecule interactions, nucleic acid-nucleic acid interactions, and nucleic acid melting. Isothermal titration calorimetry has also been used to study antibodies, cell receptors, enzymes, lipid interactions, non-biological interactions, and other reactions.

Some prior system use lasers to monitor cantilever deflection. The use of laser energy for this purpose is problematic because it tends to provide heating action that is a source of noise in the measurements. Accordingly, it is problematic to adapt microcantilever equipment for purposes of differential scanning calorimetry.

Hence there is a need for a system that overcomes one or more of the drawbacks identified above.

SUMMARY

The present disclosure advances the art by providing at least one cantilever based calorimetric analysis system.

In particular, and by way of example only, according to an embodiment, provided is a calorimetric analysis system including: at least one laser device configured to emit a beam of laser energy along a beam pathway reaching from the laser device towards a microcantilever device, the microcantilever device presenting at least one reflective target area for the beam such that the reflective target area moves in response to a heat energy function; a beam controller structured and arranged to emit the beam in a controlled manner to facilitate a differential scanning calorimetric analysis of material that is proximate the reflective target area; a detector positioned on a beam return pathway reaching from the reflective target area to the detector, the detector being configured to sense laser energy from the beam return pathway and produce a corresponding data signal that represents calorimetric data from material proximate the reflective target area; and circuitry configured to receive the data signal and process the data signal according to program logic for providing a differential scanning calorimetric analysis of the calorimetric data.

DETAILED DESCRIPTION

Before proceeding with the detailed description, it is to be appreciated that the present teaching is by way of example, not by limitation. Thus, although the instrumentalities described herein are for the convenience of explanation shown and described with respect to exemplary embodiments of a cantilever calorimetric analysis system and method, it will be appreciated that the principles herein may be applied equally in other types of analysis systems as would occur to one skilled in the relevant art and having possession of this disclosure.

Calorimetry can be defined as a measurement of the amount of heat evolved or absorbed in a chemical reaction, a change of state, or the formation of a solution. A calorimetric method of protein identification need not rely on specific binding through the use of antibodies, which typically are specifically produced for each protein. Calorimetry can be used to identify specific proteins based upon the temperature at which the specific proteins denature. Denaturing occurs when a protein's structure unfolds in response to a stimulus such as heat, alkali, or acid. Different proteins can and will denature at different specific temperatures.

The process of denaturing a protein is typically an endothermic process, absorbing heat from the surrounding liquid. However, exothermic processes, (e.g., giving off heat to the surrounding liquid), can also be measured for protein analysis. Whether the process is endothermic or exothermic depends upon the specific protein and the type of bonds creating the protein structure.

The process of denaturing can result in a change in the enthalpy of the test sample. Moreover, the change can be either positive or negative, depending on the specific protein that is denatured, and by measuring the change, identification of the protein may be established.

An index of the transition temperatures at which different proteins denature can be created. Such an index may serve as a library or table for subsequent protein identification. Specifically, the proteins in a test sample can be determined by referencing changes in the enthalpy of the test sample at specific temperatures defined by the index or table. A variety of proteins present in complex heterogeneous test solutions, such as blood or other biological fluids, can then be discovered according to protein transition temperatures detected as the test solution is heated. Measuring a protein's transition temperature can require expensive equipment and elaborate testing environments. In addition, relatively large volumes of fluid are typically used in order to establish reliable measurements.

In addition, as the protein is heated, it undergoes a series of conformational changes, and at each step of denaturing, different amounts of heat are absorbed (this being typically an endothermic process). This leads to a series of peaks appearing in the melting curve of the protein. In combination with the protein's transition temperature, these peaks can serve as a unique signature for identifying that protein or for classifying that protein as a member of a family of closely-related proteins.

Figure 1:
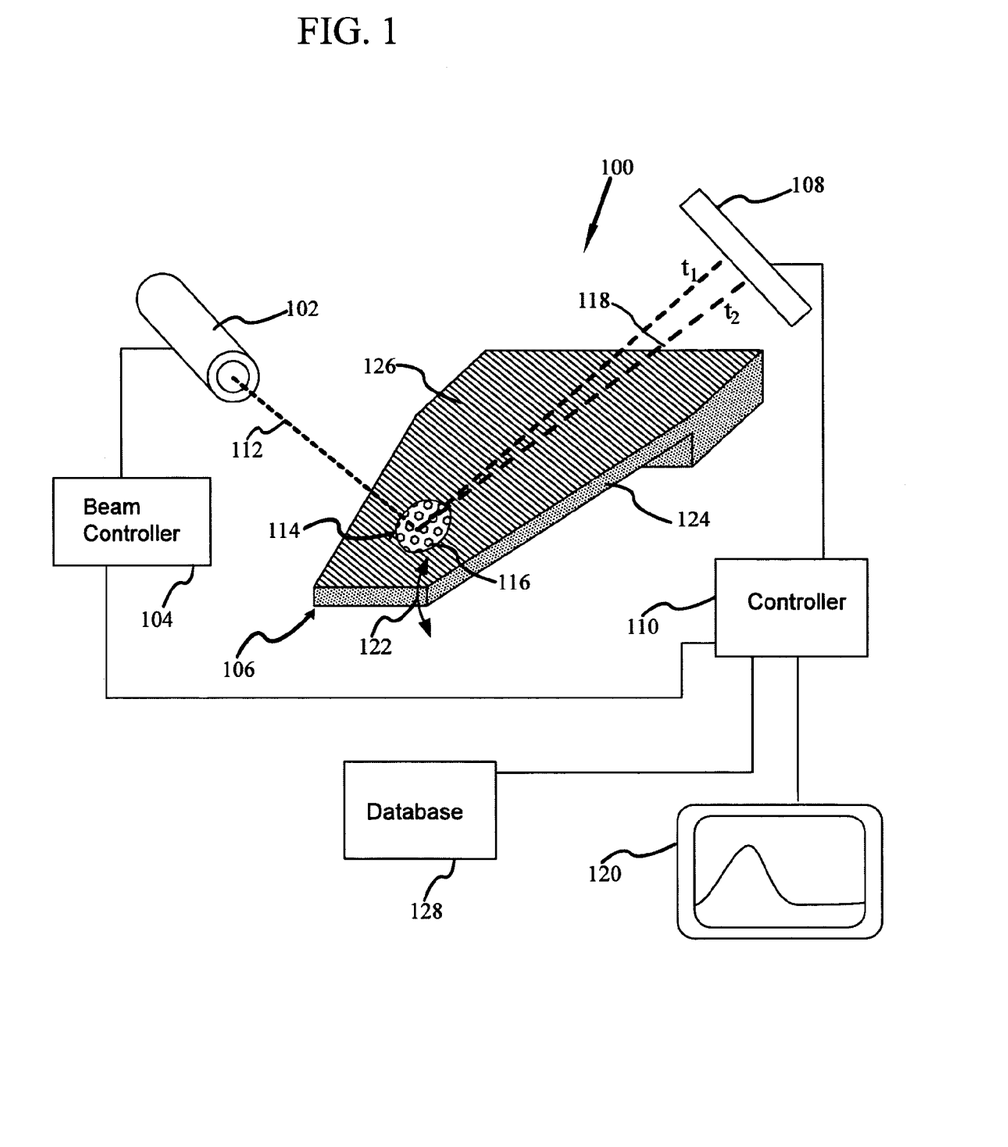
FIG. 1 is a block diagram showing an embodiment of a cantilever based calorimetric analysis system.

Referring now to the drawings, and more specifically, FIG. 1, there is shown a microcantilever calorimetric analysis system ("MCAS") 100. In the embodiment shown, MCAS 100 has at least one laser device 102, a beam controller 104, a microcantilever device 106, a detector 108 and a controller 110. The laser device 102 is configured to emit a beam of laser energy along a beam pathway 112 extending from the laser 102 to microcantilever device 106. Microcantilever device 106 provides at least one reflective target area 114. A suitable controller 110 may be comprised of analog circuitry, a digital processor, a CPU programmed with control logic, a device driver, and combinations thereof.

Beam controller 104 is structured and arranged to control emission of the laser beam in a controlled manner to facilitate a differential scanning calorimetric analysis of test material, such as analyte 116, proximate to the target area 114. More specifically, in at least one embodiment, the analyte 116 is disposed directly upon the target area 114. The target area 114 may have an area on the order of a square microns or less, up to tens of square microns. The analyte 116 may be material selected from the group consisting of a polypeptide, a polynucleic acid, an antibody, a conformational molecule, and/or combinations thereof.

In at least one embodiment the laser device 102 includes a laser writehead that is an adapted version of the laser writehead for use in CD-ROM applications such as writeable compact discs (CDs) or writeable DVDs. Moreover, the laser device 102 and beam controller 104 may be off the shelf components as are typically utilized in computer storage devices and consumer home entertainment devices. In further addition, the laser device 102 is tunable for emission of predetermined wavelengths, such as about six-hundred fifty nm and about seven-hundred eighty nm.

To aid alignment of the analyte 116 to the target area, in at least one embodiment, target area 114 is formed as a depression upon the surface of microcantilever device 106. Such a depression may be considered as the bowl of a spoon which serves to hold the analyte 116. In at least one embodiment, target area 114 may also be treated with a hydrophilic material so as to attract and/or hold analyte 116 in aqueous solution. Target area 114 may also be functionalized with a non-specific binding agent for proteins. The non-specific binding agent can be comprised of non-fat dried milk, bovine serum albumin, or any other protein configured to act as a non-specific binding agent for the proteins in the analyte 116. The non-target areas of microcantilever 106 may also be treated with a hydrophobic material. Moreover, in at least one embodiment the target area 114 is further functionalized by binding with the analyte 116.

Bending or deflection of the microcantilever device 106 in response to heat energy causes the return pathway 118 to shift over time. This is illustrated, by way of example, as pathway $t_1$ and pathway $t_2$, indicative of the return pathway 118 at different times. The return pathway 118 terminated by impinging upon the detector 108. In at least one embodiment the detector 108 is a photo detector, and more specifically is a grid array of charged-coupled devices that are tuned for the detection of laser energy. Detector 108 is configured to sense laser energy from the return pathway 118 and produce corresponding data signals that are representative of the calorimetric data from the analyte 116 proximate to the reflective target area 114.

The controller 110 is provided with program logic for differential scanning calorimietry analysis on the basis of data signals from the detector 108. Calorimetry analysis output from the controller 110 is provided to a recording device and/or display 120. In at least one embodiment, the controller 110 is in electrical communication with a database 128. The database 128 may be a separate component as shown, or located in one or more memory chips integrated with the controller 110. The database 128 holds identification information of known material parameters, such as for example the identity of specific proteins and their respective denaturing temperatures. By comparing the data signals received from the detector 108 with the database information, the controller 110 in at least one embodiment is operable to specifically identify elements such as proteins present in the analyte 116.

It is appreciated that microcantilever device 106 may include an array of microcantilever structures, each of which deflect over range 122 due to a bimaterial bending moment. Generally microcantilever device 106 is rectangular. As shown microcantilever device 106 has a base 124, that by way of example may be made of silicone nitride, and a cap 126, that by way of example may be made of gold or another bimaterial with respect to the base 124. Since bimaterials differ in their respective coefficients of thermal expansion, a temperature change is associated with a volumetric change that induces a bending moment and associated deflection over range 122.

The bending moment of microcantilever device 106 is designed to produce cantilever deflection at subnanometer levels. The low thermal mass of the base 124 and cap 126 allows deflection in response to temperature changes of about $10^{-6}$ K for heat exchanges such as protein denaturization. The thermal response of the analyte 116 may be modeled mathematically by use of Stoney's formula.

Microcantilever device 106 can be about fifteen microns long and about five microns wide. The microcantilever 106 can be formed from semiconductor materials through a series of known etching processes. It is understood and appreciated that the microcantilever devices 106 may be formed having a wide range of sizes, the size being limited only by the limits of lithography. Current limits create a minimum dimension of about 0.1 microns, but future improvements in lithography and MEMS construction may further reduce the size of microcantilever devices.

MCAS 100 can be used to both heat analyte 116 and to accurately measure any changes in enthalpy which occur in analyte 116. Typically where a laser is used to measure deflection of a cantilever based on thermal change, the laser is specifically selected and controlled so as not to contribute a significant or measurable heat to the microcantilever device and/or any materials present upon or proximate to the microcantilever device. Moreover, the laser is relied upon as a measurement device and is controlled so as not to alter or affect the testing environment.

In the instance case of the embodiments set forth herein, the laser is specifically selected and operated with sufficient power so as to provide a known quantity of heat energy to the analyte 116. More specifically, the beam controller 104 controls laser 102 to emit a series of laser beam pulses, each pulse having a specific duration and peak amplitude of intensity.

The amount of temperature rise caused by each pulse of applied heat and its spatial profile will depend on the design of the microcantilever (shape, materials used, etc.). This can be understood both by thermal modeling as well as by calibration on finished microcantilevers. At any rate, the result will be that each pulse's amplitude and duration will lead to a well-known and precise amount of temperature rise in the sample. Moreover, as the amount of temperature rise caused by each pulse is known to the system, the heat absorbed during denaturing and the ultimately released provides a specific series of peaks appearing in the melting curve of the protein, which in turn serves to identify the protein.

These pulses are applied directly to the analyte 116 such that the heat energy is provided directly to the analyte 116 as well. Such direct application of heat energy is advantageous over other calorimetric processes which rely on a heat source such as a resistor to provide heat which must propagate by conduction to the analyte 116. Moreover, heat transfer issues and latency between heat generation and reaction by the analyte 116 are reduced significantly as beam controller 104 and laser 102 permit MCAS 100 to apply localized heat directly to the analyte 116. As heat generation occurs only at target area 114 and the issue of heat transfer from another source is all but eliminated, the short pulses of laser energy and speed of detecting deflection permit the MCAS 100 to be quasi-adiabatic, since parasitic heat leaks from other sources will be slower than the phase transition and thermal transients of interest, allowing for more accurate testing.

The heat capacity of a substance is the amount of heat required to change its temperature by one degree. Due to the extremely small mass of the microcantilever 106, the microcantilever 106 has a very small heat capacity, which enables small changes in temperature to be measured within a span of a few microseconds. As described above, the localized application of heat via the pulses of laser energy directly to the analyte 116 further reduces test latency by eliminating the need for heat transfer via conduction. In at least on embodiment, a typical measurement can be done in five to fifty microseconds.

A shorter time span can be accomplished by further reducing the size of the microcantilever 106. The rapid measurement of changes in temperature greatly increase the accuracy of the temperature measurements and allow for a substantially adiabatic system, where the influences of the substructure or container supporting the microcantilevers can be assumed essentially negligible. The microcantilever's small size, combined with the laser heating system, enable embodiments to have temperature accuracy desirable to detect changes in enthalpy in small test solutions (i.e., small quantities of analyte 116) which occur when specific proteins denature.

The application of heat energy by the laser beam along pathway 112 is effectively a surface event upon microcantilever device 106. The accumulation of laser induced heat energy applied to analyte 116 will result in a change of state of the analyte 116. For example, where the analyte 116 is a protein the application of a specific amount of heat will result the denaturing of the protein. As the protein denatures it changes the surface stress applied to the microcantilever 106. In at least one embodiment, the denaturing protein releases additional energy in the form of heat which induces different thermal expansion between the base 124 and cap 126 of microcantilever device 106, and thus deflection of returning pathway 118.

As beam controller 104 and laser 102 are providing controlled pulse energy to heat analyte 116, a linear progression of the return pathway 118 will be detected by detector 108. The event of a change of state, e.g., the denaturing of a protein, will result in a sudden and pronounced shift of the return pathway 118 as detected by detector 108. This detection results in a data signal representing the calorimetric data from the analyte 116.

In at least one embodiment, as further described below, MCAS 100 includes at least two microcantilever devices 106, a control microcantilever device 106 having a target area 114 with no analyte 116 present, and a test microcantilever device 106 having analyte 116 disposed proximate to the target area 114. The relative heating of the test microcantilever device 106 provided by the pulsed laser beam and change of state events within the analyte 116 resulting in the evolution or absorption of heat may be compared to detect one or more calorimetric events.

For the embodiment of MCAS 100 as shown in FIG. 1, the return beam pathway 118 from the same laser beam provided along pathway 112 to heat analyte 116 is received by detector 118. Moreover, a single beam controller 104 and laser device 102 are used for both heating the analyte 116 and measuring the deflection of microcantilever 106.

Figure 2:
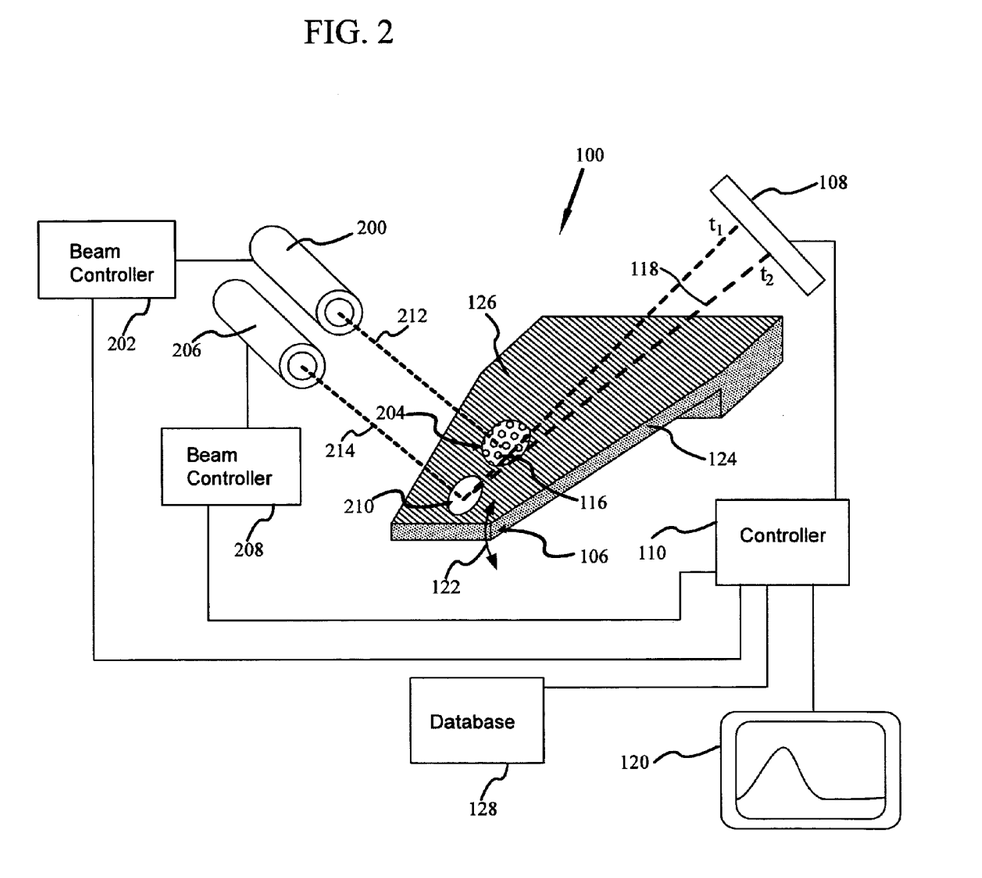
FIG. 2 is a block diagram showing an alternative embodiment of a cantilever based calorimetric analysis system.

FIG. 2 illustrates an alternative embodiment of MCAS 100 wherein a first laser 200 and first beam controller 202 are used to apply heat to analyte 116 provided in a first target area 204, and a second laser 206 and second beam controller 208 are used with second target area 210 to detect and measure heat induced deflection of microcantilever device 106. With respect to the embodiment shown in FIG. 2, first laser .200 is substantially identical to laser device 102 shown and described with respect to FIG. 1 above.

Laser device 200 is configured to emit a beam of laser energy along a beam pathway 212 extending from the laser 200 to first target area 204. As in FIG. 1 and laser device 102, this laser beam of energy is provided as a series of pulses of known duration and specific amplitude so as to provide heat energy to the analyte 116 disposed adjacent to target area 204. Laser device 206 is configured to emit a beam of laser energy along a beam pathway 214 extending from the laser 206 to the second target area 210 which is substantially free of analyte 116.

Bending or deflection of the microcantilever device 106 in response to heat energy developed at target area 204 causes the return pathway 118 to shift over time. This is illustrated, by way of example, as pathway $t_1$ and pathway $t_2$, indicative of the return pathway 118 at different times. As in FIG. 1, the return pathway 118 terminated by impinging upon the detector 108.

The laser energy provided by laser 206 may or may not be provided as a continuous beam or as a series of pulses. It is understood and appreciated that laser 206 is operated by beam controller 208 with such a low power amplitude as to effectively provide no meaningful heat energy to microcantilever 106. More specifically, laser 200 serves to provide heat the analyte 116 while laser 206 serves to provide the reference beam that is monitored by detector 108 to detect deflection of the microcantilever representative of calorimetric data from the analyte 116.

The embodiment of FIG. 2 may enjoy certain advantages over the embodiment of FIG. 1. For example, as the laser energy from laser 206 is not falling upon analyte 116, calibration circuitry operable to correct the data signal from the detector for beam scattering may be significantly reduced. Similarly, as the laser energy from laser 206 is not falling upon analyte 116, beam absorption by analyte 116 and thus corrective calibration is again reduced.

In at least one embodiment, the first and second beam controllers may be a combined beam controller, however they have been illustrated separately for ease of discussion. Further, the relative size and placement of first target area 204 and second target area 210 have been rendered for ease of illustration and discussion, and not to suggest or imply a limitation. It is further understood and appreciated that first target area 204 may be substantially identical to target area 116 as described above with respect to being a structural depression and/or functionalized by treatment with hydrophilic material.

Figure 3:
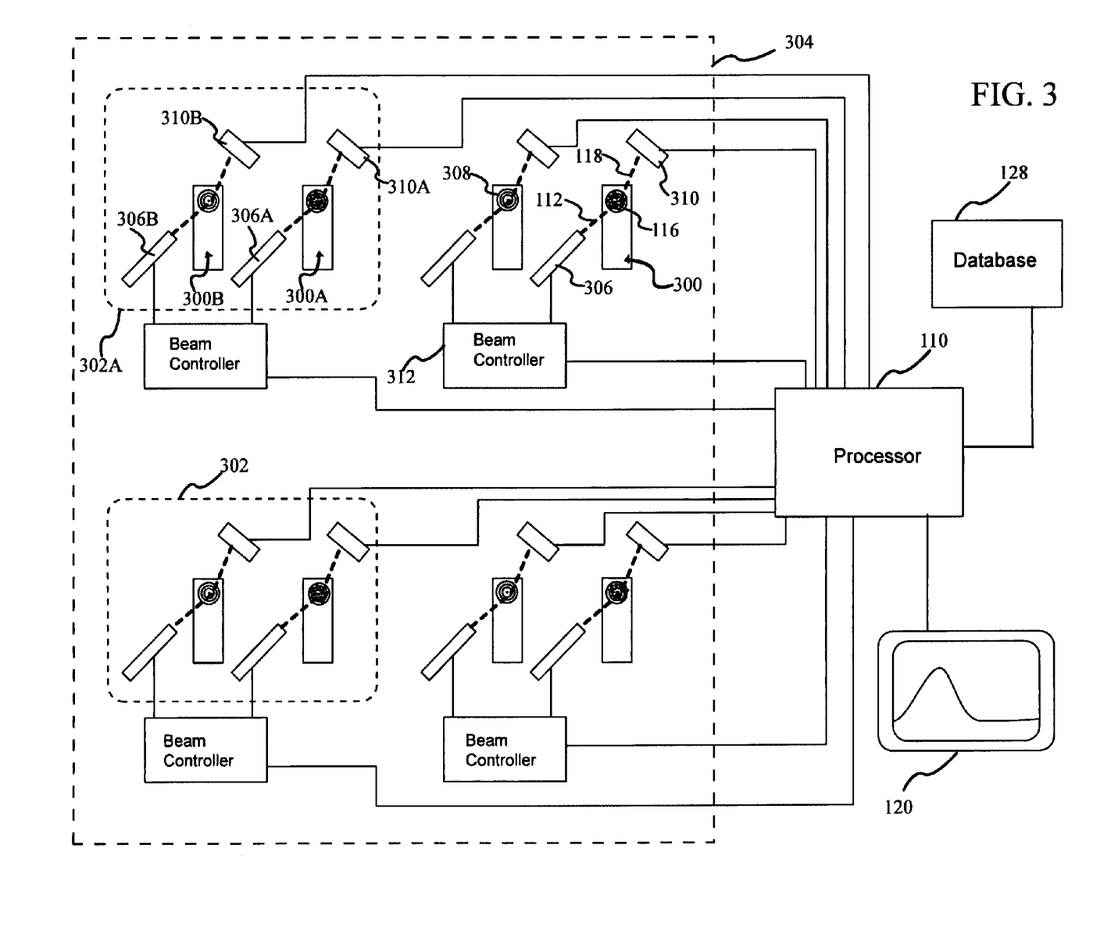
FIG. 3 is a block diagram showing an array of microcantilever devices in another embodiment of a cantilever based calorimetric analysis system.

As shown in FIG. 3, in at least one embodiment, MCAS 100 has a plurality of microcantilever devices 300. In at least one embodiment the plurality of microcantilever devices 106 are arranged as pairs 302, arranged in an array 304. As shown, each microcantilever device has a single associated laser 306, target area 308 and detector 310, much as is shown in FIG. 1. It is understood and appreciated that microcantilever devices 300 may be as shown in FIG. 2, having two lasers and two target areas. FIG. 3 has been rendered to depict a single laser and target area to avoid undue confusion, and is not intended to infer a limitation.

For each pair, i.e., pair 302A one microcantilever device serves as a test microcantilever 300A while the other serves as a control microcantilever 300B. In an alternative embodiment, a control microcantilever may be paired with several test microcantilevers. Beam controller 312 operates associated lasers 306A and 306B contemporaneously. Detector 310B therefore provides a control data signal corresponding to the applied heat provided by the laser beam emanating from laser 306B. Detector 310A provides a test data signal which will includes the calorimetric data from the analyte 116. In at least one embodiment, controller 110 evaluates the difference between the control data signal and the test data signal and so identifies differences in temperature, i.e., $\Delta T$, which are indicative of a change in heat capacity, i.e. $\Delta C$, indicative of at least one calorimetric event occurring in the analyte 116.

As illustrated, the detectors and beam controllers are electrically connected to the controller. As such, redundant simultaneous testing of analyte 116 may be performed. By combining the data signals from the plurality of test detectors 310A, the signal to noise ratio of the data signal is enhanced.

Such enhancement to the data signal permits even greater accuracy in the calorimetric analysis achieved by MCAS 100.

Where the analyte 116 is provided in a fluid, which may be liquid or gas, as a test solution to test microcantilevers 300A, a buffered fluid with similar characteristics to the test solution is provided to control microcantilevers 300B. These similar characteristics can include having a similar temperature, pH, salt concentration, transparency, and/or other such characteristics. The similar characteristics should allow the buffered solution to have substantially the same thermal properties as the test solution.

For embodiments in which a single laser configuration is utilized with each microcantilever 300 (providing localized heat to the target area 308 and being received by detector 310), the use of a buffered solution provides a baseline between the control and test microcantilevers 300A, 300B, wherein the effect of beam scattering and or absorption upon the resulting data signal is effectively minimized.

Electrically coupled to a database 128, controller 110 may further identify one or more components of analyte 116 based comparing the data signals to specific information recorded in the database 128. Calorimetry analysis output from the controller 110 is provided to a recording device and/or display 120.

In at least one embodiment, a calibration circuit is provided as part of MCAS 100. Such a calibration circuit may include a specific pair of microcantilevers, the control microcantilever maintained as clean—free from either analyte or buffered solution. Calibration is performed by providing test solution or buffered solution to the test microcantilever and comparing the detected reflected laser energy with the reflected laser energy from the clean control microcantilever.

Figure 4:
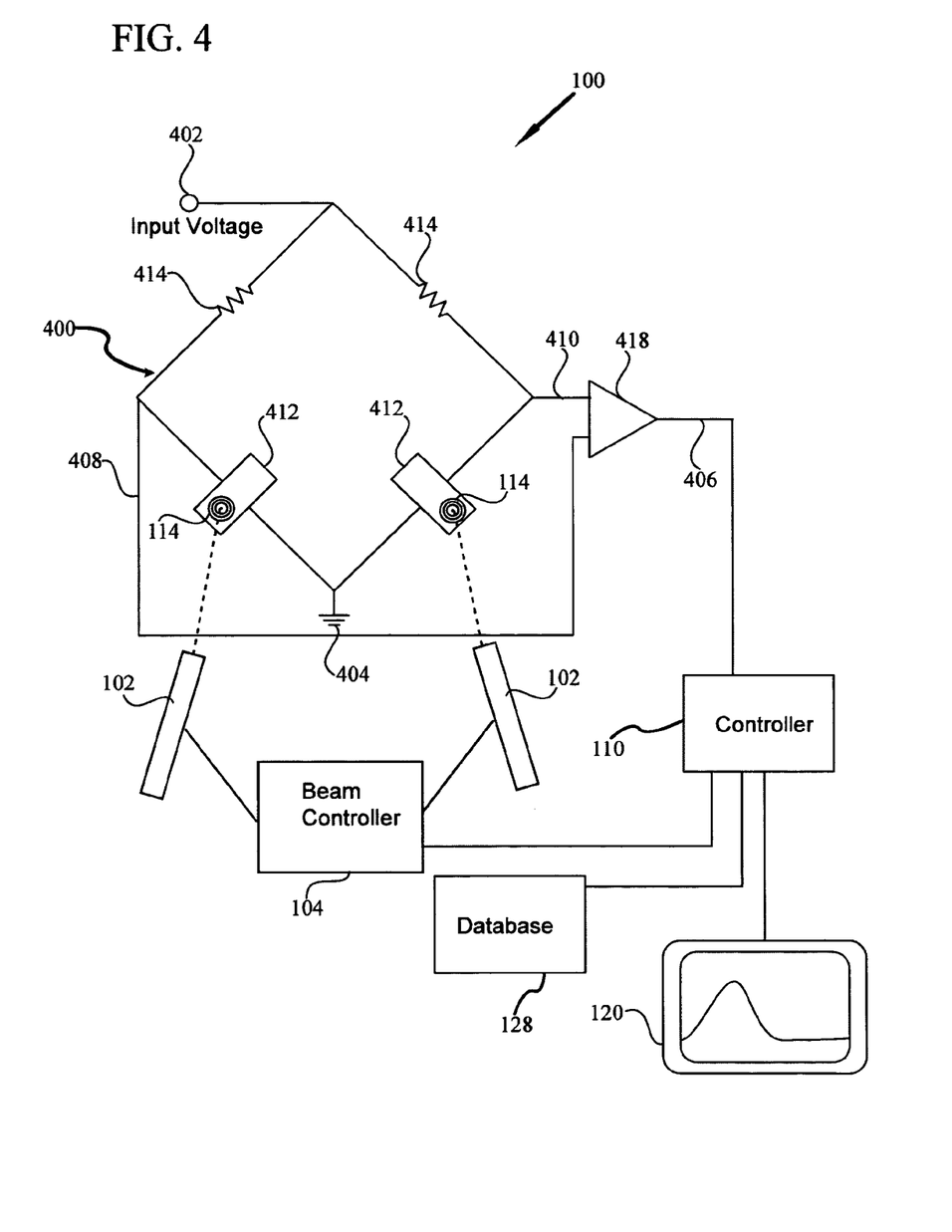
FIG. 4 is a block diagram of cantilever based calorimetric analysis system according to yet another embodiment.

FIG. 4 illustrates yet another alternative embodiment for MCAS 100 wherein the laser heated microcantilever devices 106 are arranged in a Wheatstone bridge configuration 400.

Due to their sensitivity, Wheatstone bridge circuits are advantageous for the measurement of resistance, inductance, and capacitance. A Wheatstone bridge circuit configuration consists of four resistive elements electrically coupled in a diamond orientation 400. An input voltage 402 is applied between the input 402 and ground 404 of the diamond, and output voltage 406 is measured between two measurement taps 408 and 410.

When the output voltage, the potential difference between 408 and 410, is zero, the bridge is said to be balanced. One or more of the legs of the bridge may be a resistive element, such as a microcantilever device 412 substantially similar to microcantilever device 106 as discussed above. To provide resistive qualities to the microcantilever device 106 may be formed with doped semiconductor materials (i.e. doped silicon nitride for the base) to provide microcantilever device 412.

The other legs of the bridge are simply completion resistors 414 with resistances set to be substantially equal to that of the microcantilevers 412 when the bridge is balanced. The completion resistors 414 may also be potentiometers, enabling each completion resistor to be adjusted to allow the bridge to be balanced. Each microcantilever device 412 provides a target area 114 as described above. A beam controller 104 controls a laser 102 to provide a beam of laser energy along a beam pathway 416 reaching from the laser 102 to the target area 114 of each microcantilever 412.

As the beam controller 104 directs the laser 102 to provide pulsed laser energy to the target area 114, the resistance of at least one leg will change due to a change in the temperature of the doped microcantilever device 412, and the previously balanced bridge can become unbalanced. This unbalanced state can cause a difference in potential to appear across the middle of the bridge. In at least one embodiment, this difference is measured using a lock-in amplifier 418. The lock in amplifier provides output data 406 that can be sent to a controller 110 or other control circuitry that is configured to receive the output and process the output data 406 according to program logic for providing a differential scanning calorimetric analysis. The processed data may in turn be sent to a recording device or output display 120.

A change in temperature in the analyte 116 present upon the target area will result in a change of temperature and thus deflection of the microcantilever device 412. Moreover, a change in temperature in the analyte 116 due to a chemical reaction or denaturing proteins, can be detected by the microcantilever device 412. This change in temperature can alter the resistance of the microcantilever device 412. A small change in the resistance in the microcantilever device 412 can cause the Wheatstone bridge 400 to become unbalanced, causing a voltage to appear across the middle of the bridge. This voltage difference can induce a current which can be accurately detected by lock-in amplifier 418.

Accurately measuring small changes in DC current can be difficult. Lock-in detection using a lock-in amplifier can be used to increase the accuracy of the measurement. Lock-in detection can be used to perform a quasi-DC measurement at a non-zero frequency with a smaller bandwidth than DC. The smaller bandwidth can reduce the amount of noise on the signal.

Each Wheatstone bridge circuit 400 can be balanced at room temperature, or a series of temperatures, by adjusting the resistance of the completion resistors. The completion resistors can be manually or electrically adjusted. A computer, such as controller 110, can be used to adjust the completion resistors to a predetermined value for a given temperature.

The Wheatstone bridge circuit 400 configuration can be used to measure the heat capacity in a test solution. Heat capacity C is the derivative of energy E with respect to temperature T, leading to the equation:

$$C = \frac{dE}{dT}$$

It has been found that resistance R is linear with respect to temperature T. Power can be input for a time $\tau$. The change in resistance $\Delta R$ of the microcantilevers in the bridge circuit can be determined by using the lock-in detector to measure the change in current, and determining the resistance with Ohm's law, $$\Delta R = \frac{V}{\Delta I},$$

where V is the DC voltage applied between the top and bottom of the bridge circuit. Alpha can be defined as the temperature coefficient of resistivity, with $\alpha = dR/dT$, the change in resistance per change in temperature. Change in heat capacity, $\Delta C$, can then be defined as:

$$\Delta C = \frac{P \times \tau \times \alpha}{\Delta R}$$

In an example embodiment, the microcantilever can have a resistance of about 1600 ohms. Two leads can be connected to each microcantilever to measure current and voltage. Alternatively, four leads can be connected to each microcantilever, with two leads used to measure current and two leads used to measure voltage. Using four leads, the effects of the leads in the measurement can be minimized. A typical value of dR/dT for a microcantilever can be five (5) ohms/K, or five (5) ohms per degree Kelvin.

A Wheatstone bridge having two matched resistors and two microcantilevers, each with a resistance of 1600 Ohms, can have a resistance of 3,200 Ohms across the bridge. The current is equal to the voltage divided by the resistance. At 1 volt, the current is about three hundred microamps. Power is equal to the voltage times the current, or three hundred microwatts. A change in resistance $\Delta R$ of 2 ohms can be realized. Thus, the system can have a sensitivity capable of measuring a change in heat capacity of:

$$\Delta C = \frac{300 \times 10^{-6} W \times 100 \times 10^{-6} S \times 5\, Ohms/K}{2\, Ohms} = 75 nJ/K$$

With respect to FIGS. 1~4, it is appreciated that for calorimetric analysis, the preferred location for the analyte 116 is upon the target area 114, 204 (and target area 308 of test microcantilever 300A). To achieve such placement, microcantilever 106 may be dipped in a solution containing analyte 116 and then extracted, such that a droplet of analyte 116 remains substantially proximate to the target area.

In one embodiment, calorimetric analysis is immediately performed upon the analyte 116 in aqueous suspension. Such a process may be termed a wet process. In an alternative embodiment, the aqueous material is permitted to evaporate, thus depositing analyte 116 upon target area 114, 204. As the size of the droplet providing analyte 116 is quite small, evaporation occurs rapidly. Such a process is termed a dry process. In either case it is appreciated that the quantity of solution containing analyte 116 may be quite small. Use of a small quantity of analyte 116 which is known to be substantially in the preferred location for testing advantageously shortens the time required for the testing as no latency is required for the analyte 116 to migrate through a large volume of solution.

In an alternative embodiment, analyte 116 may be provided to the target areas by micro fluidic channels disposed within each microcantilever. An unknown analyte 116 may be injected into the test channels in a test solution while a buffered solution is injected into control channels, the test and control channels appropriate matched to test and control microcantilevers as shown in FIG. 4.

It is also understood and appreciated that the one or more microcantilever devices 106 of MCAS 100 may be immersed in a test solution while the calorimetric analysis is performed. More specifically, the test microcantilever devices 106 intended to receive analyte 116 upon the target area for the heating laser device may remain in the test solution, the heating laser being directed to pass through the test solution and strike the target area. Such submerged testing may involve further calibration of the associated lasers and detectors due to diffraction occurring as the laser light enters and exits the test solution. As such either the wet or dry testing process discussed above may be more preferred embodiments over a submerged embodiment.

Figure 5:
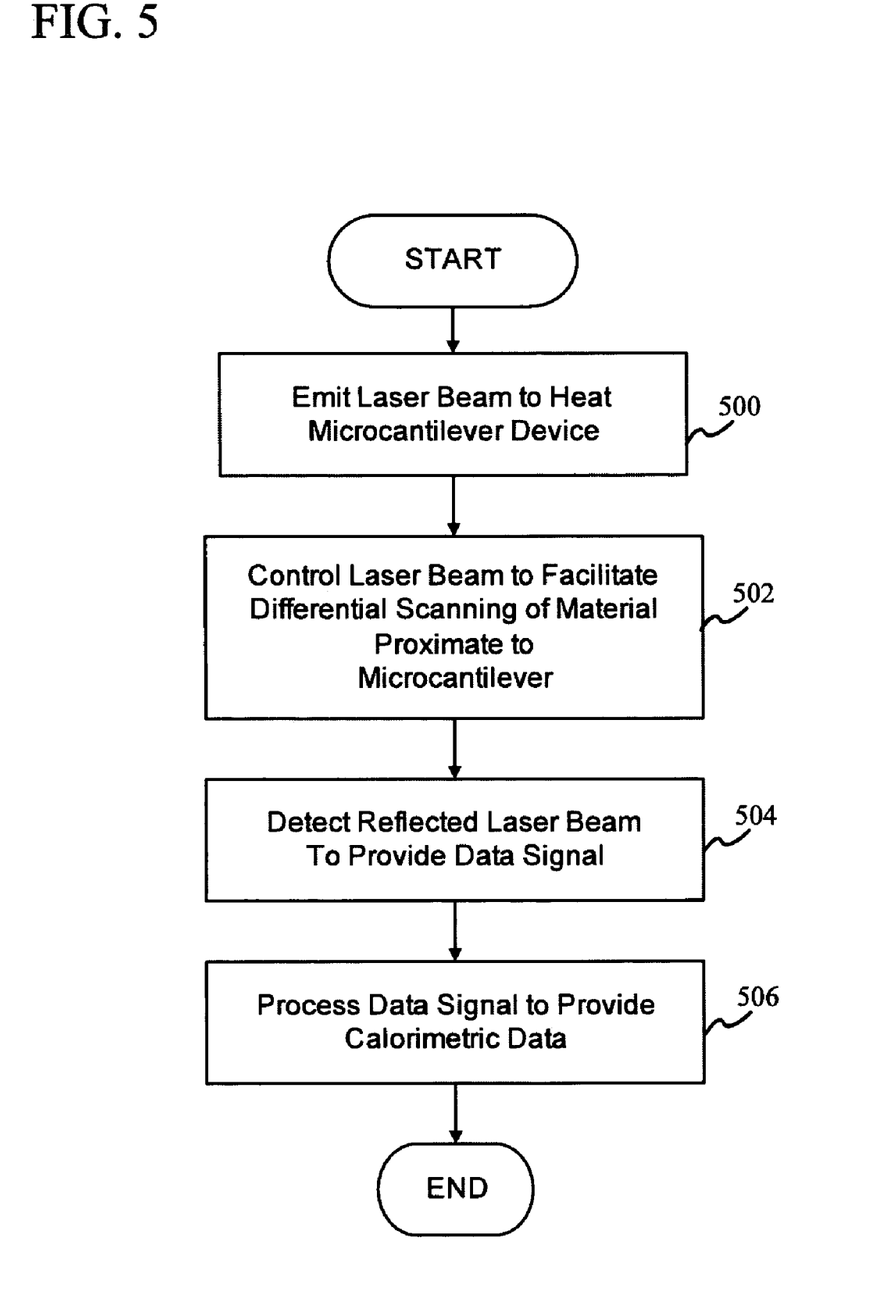
FIG. 5 is a flow diagram illustrating at least one method of use for a cantilever based calorimetric analysis system according to at least one embodiment.

In the above embodiments described with respect to FIGS. 1~4, heating of the target area 114, and more specifically the analyte 116, is not generally performed while the microcantilever 106 is immersed in the test solution. FIG. 5 presents yet another embodiment.

Having described the physical structure of several embodiments for MCAS 100, additional advantages of the alternative structures may well be appreciated through the discussion of an embodiment for at least one method of use. This description is provided with reference to the flowchart provided as FIG. 5, and the embodiments shown and described in FIGS. 1~3. It will be appreciated that the described method need not be performed in the order in which it is herein described, but that this description is merely exemplary of one method of using the MCAS 100.

As described above with respect to FIGS. 1~3, a MCAS 100 is provided an analyte 116 is deposited upon the surface of the microcantilever, and more specifically proximate to the target area 114 (see FIGS. 1~2). The beam controller directs the laser device to emit laser energy to heat the target area 114 of microcantilever 106, as in block 500.

To facilitate the differential scanning of the analyte 116, the beam controller controls the laser device to emit the laser energy as pulses of known duration and peak amplitude, as in block 502. Such pulses permit specific calculation of the heat energy applied with greater accuracy then with a continuous beam of laser energy.

At least a portion of the applied laser energy beam is reflected by the reflective target area to the detector. The detector detects the reflected laser beam and provides a data signal representative of the calorimetric data from the analyte 116, as in block 504. The controller processes the data signal according to program logic for providing a differential scanning calorimetric analysis of the calorimetric data, as in block 506.

As discussed above, in at least one embodiment the MCAS 100 provides at least one test microcantilever and at least one control microcantilever. Moreover, in at least one embodiment, heat in the form of a pulsed laser energy beam is applied contemporaneously by the beam controller to both a test microcantilever and a control microcantilever. Comparison between the resulting test data signal and the control data signal permits enhanced calorimetric analysis of the calorimetric data.

The MCAS 100 can be useful in performing microcalorimetric measurements to determine one or more proteins in a heterogeneous test solution. Using microcantilevers having an extremely small size and weight, quasi-adiabatic measurements can be performed, allowing measurements with sensitivities of a few nJ/K to be detected. Such sensitivity can allow the system to rapidly detect less than 1 microgram of protein attached to a cantilever tip in the heterogeneous test solution. The MCAS 100 can be configured to be relatively inexpensive and can analyze test samples almost instantaneously. The MCAS 100 fulfills a long sought need for a system capable of inexpensively, quickly, and accurately detecting a plurality of non-specific proteins in a heterogeneous solution.

Changes may be made in the above methods, systems and structures without departing from the scope thereof. It should thus be noted that the matter contained in the above description and/or shown in the accompanying drawings should be interpreted as illustrative and not in a limiting sense. The following claims address all generic and specific features described herein, as well as all statements of the scope of the present method, system and structure which, as a matter of language, might be said to fall therebetween.

What is claimed is:

1. A cantilever based calorimetric analysis system comprising:
   a first laser device configured to emit a first beam of laser energy along a first beam pathway reaching from the first laser device towards a microcantilever device;
   a second laser device configured to emit a second beam of laser energy along a second beam pathway reaching from the second laser device towards the microcantilever device;
   the microcantilever device presenting a first surface having a first target area for the first beam and the first surface also having a second reflective target area for the second beam, such that the first target area moves in response to a heat energy function, the second target area reflecting the second beam along a beam return pathway;
   a detector positioned on the beam return pathway reaching from the second target area to the detector;
   the detector being configured to sense laser energy from the beam return pathway and produce a corresponding data signal that represents calorimetric data from material proximate the first target area and receiving heat energy directly from the first beam; and
   circuitry configured to receive the data signal and process the data signal according to program logic for providing a differential scanning calorimetric analysis of the calorimetric data.

2. The cantilever based calorimetric analysis system of claim 1, wherein the first laser device is a heating laser device structured and arranged to provide heat energy in the form of pulsed laser energy to the first target area, each pulse having a specific duration and peak amplitude of intensity, and wherein the second laser device is structured and arranged to provide no measurable heat energy to the second reflective target area.

3. The cantilever based calorimetric analysis system of claim 1, further comprising material proximate the first target area, the material being sufficiently close to the first target area for inducing relative motion of the microcantilever device on the basis of calorimetric interaction between the material and the beam.

4. The cantilever based calorimetric analysis system of claim 3, wherein the material is selected from the group consisting of a polypeptide, a polynucleic acid, an antibody, a conformational molecule, and combinations thereof.

5. The cantilever based calorimetric analysis system of claim 4, wherein the first target area is functionalized by binding with the material.

6. The cantilever based calorimetric analysis system of claim 1, wherein the first target area further includes a depression structured and arranged to hold the material.

7. The cantilever based calorimetric analysis system of claim 1, wherein the laser device includes a laser writehead that is an adapted version of a laser writehead for use in CD-ROM applications.

* * * * *

UNITED STATES PATENT AND TRADEMARK OFFICE
CERTIFICATE OF CORRECTION

PATENT NO. : 7,429,125 B2  Page 1 of 1
APPLICATION NO. : 11/270690
DATED : September 30, 2008
INVENTOR(S) : Manish Sharma et al.

It is certified that error appears in the above-identified patent and that said Letters Patent is hereby corrected as shown below:

On the face page, in field (57), under "Abstract", in column 2, line 10, delete "single" and insert -- signal --, therefor.

Signed and Sealed this

Thirtieth Day of December, 2008

JON W. DUDAS
*Director of the United States Patent and Trademark Office*